(12) United States Patent
Cordray

(10) Patent No.: US 7,687,078 B1
(45) Date of Patent: *Mar. 30, 2010

(54) METHOD OF TREATMENT

(76) Inventor: Scott Cordray, 1145 S. Utica, Tulsa, OK (US) 74104

( * ) Notice: Subject to any disclaimer, the term of this patent is extended or adjusted under 35 U.S.C. 154(b) by 1141 days.

This patent is subject to a terminal disclaimer.

(21) Appl. No.: 11/243,574

(22) Filed: Oct. 5, 2005

(51) Int. Cl.
*A01N 59/08* (2006.01)
*A61K 33/14* (2006.01)
*A61K 33/06* (2006.01)
*A01N 43/04* (2006.01)

(52) U.S. Cl. ............ 424/678; 424/679; 424/681; 424/697; 514/57

(58) Field of Classification Search ............ None
See application file for complete search history.

(56) References Cited

U.S. PATENT DOCUMENTS

| | | | | | |
|---|---|---|---|---|---|
| 5,466,680 | A | * | 11/1995 | Rudy | 514/57 |
| 5,741,525 | A | * | 4/1998 | Larsen | 424/616 |
| 5,778,886 | A | * | 7/1998 | Shihata | 128/832 |
| 7,186,417 | B1 | * | 3/2007 | Siegel et al. | 424/405 |

FOREIGN PATENT DOCUMENTS

EP 0937453 * 8/1999

* cited by examiner

*Primary Examiner*—Yvonne L Eyler
*Assistant Examiner*—Tigabu Kassa
(74) *Attorney, Agent, or Firm*—John Lezdey & Assoc

(57) ABSTRACT

Compositions for treating anal and vaginal inflammations while maintaining normal vaginal floral activity utilizing magnesium and alkali metal salts at an acidic pH.

7 Claims, No Drawings

METHOD OF TREATMENT

FIELD OF THE INVENTION

The present invention is related to the treatment of anal and vaginal inflammation. More particularly, there is provided a method of treatment of inflammation in the vaginal cavity while maintaining normal vaginal floral activity and to treat anal/vaginal inflammation with magnesium and alkali metal salts.

BACKGROUND OF THE INVENTION

The most common anorectal irritation or inflammation is caused by hemorrhoids. This condition can be caused by poor sanitary conditions, constipation, bacterial infection, etc. Common treatment is with sanitary wipes, suppositories and gels.

Other anal inflammations are involved with anal fissures, anorectal fistula and proctitis.

One of the main disciplines of medicine is the treatment of the female reproductive system for the prevention, treatment, mitigation, diagnosis, and cure of diseases, and the prevention of conception. Usually, this involves the delivery of active agents to the vaginal cavity and its environs. Systems to affect the delivery of such agents are usually in the form of gels, foams, creams, or suppositories and quick dissolving tablets.

The vaginal cavity is subject to conditions which render it as a target for disease and infection; however, it is extremely difficult to deliver an active agent to this area for an extended period of time. The vaginal cavity exhibits an aqueous environment containing secreting glands whose fluids create an acidic pH in the range of 3.5 to 5.5. The environment of the vagina is conducive to the growth of bacteria, fungi, yeast and other microorganisms since it is warm, moist, and dark. It is also the vestibule for menstrual debris and residual seminal fluid from sexual intercourse. The crevices of the vaginal cavity facilitate the retention of undesirable bacteria, fungi, yeast, and other microorganisms as well as the debris from menstruation and sexual intercourse. The vaginal cavity is also subject to considerable physical deformation, such as during sexual intercourse or the insertion of tampons.

Infectious diseases and other inflammatory conditions affecting the vaginal mucosa and often secondarily involving the vulva are commonly referred to as vulvovaginitis. Physicians and investigators often believe that the normal vaginal flora has a nice role in protecting the vagina and contiguous tissues from various microorganisms that are causes of vulvovaginitis.

Most vulvovaginitis and symptomatic vaginal discharges are caused by bacteria, usually *Gardnerella vaginalis* in combination with various anaerobes. Protozoa (*Trichomonas vaginalis*) cause one third of all cases. *Candida* is a frequent cause in pregnant women and diabetics, and occasionally oral contraceptives increase susceptibility. *Candida* also causes symptoms in women who do not have the risk factors of diabetes, pregnancy, and hormonal therapy.

Other less common causes of vulvovaginitis are other bacteria (e.g. *Neisseria gonorrhoeae*, members of the *Chlamydia* and Mycoplsma groups, streptococci, *Escherichia coli*, and staphylococci), foreign bodies, viral infections (herpes simplex and HIV infections), pinworms (*Enterobius vermicularis*), fituals, radiation, and tumors of the genital tract. Frequent douching, especially with chemicals, may disturb normal vaginal milieu. Deodorant sprays, laundry soaps and fabric softeners, and bath water additives may cause vulvar irritation and inflammation. Tight, nonporous, nonabsorbent underclothing, as well as poor hygiene, may foster fungal and bacterial growth. Occasionally, sensitivity to spermicides, coital lubricants, or latex in a diaphragm or condom causes irritation and inflammation.

The pH of a healthy vaginal is mildly acidic (pH 3.5-4.5) and this acidity is thought to be generated by the production of lactic acid by lactobacilli, which form a major component of the healthy vaginal flora. Together with other factors, this acid pH is widely recognized to prevent overgrowth of undesirable endogenous microbes (Candida, harmful anaerobes, and bacteria that may cause urinary tract infections) and encourages the continued dominance of lactobacilli which, in addition to mild acidity, provides other protective mechanisms such as production of hydrogen peroxide which aids in modulating cell growth of other microbial species.

It is also known that sperm are inactivated by the mild acidity of the healthy vagina, and acid substances have been used as home made vaginal contraceptives for centuries. More recently, it has been recognized that many sexually transmitted disease pathogens and most or all enveloped STD (sexually transmitted disease) viruses (Kempf 1001, Martin 1985) including herpes simplex virus, cytomegalovirus, and human immunodeficiency virus, are also inhibited or inactivated by mild acidic pH. However, semen contains a potent alkaline buffering capacity that neutralizes the vaginal acidity for a period of many hours after intercourse. The alkaline buffering capacity enables sperm to swim from the vagina into the cervix and upper reproductive tract.

Unfortunately, STD pathogens in genital secretions can also exploit this period of neutral vaginal pH, since it allows time for them to reach and infect their target cells. If this semen-induced neutralization of vaginal acidity could be promptly and reliably overcome, both contraception and STD prevention could be achieved by a method that closely mimics the normal physiological state of the vagina.

In addition, the elevated pH also allows certain strains of *Staphylococcus aureus* to produce shock toxin I, whereas production of this toxin is completely inhibited at acidic pH 5.0 (Schlievert 1983). Thus, loss of protective acidity may result in staphylococcal toxic shock syndrome, candida vaginitis, bacterial vaginosis, or urinary tract infection.

SUMMARY OF THE INVENTION

The present invention relates to method for treating anal and vaginal inflammation while maintaining a proper pH to enhance the protection of vaginal flora. More particularly, there is provided a method for administrating an effective amount of a composition comprising
  a) about 0.5 to 10% by weight, preferably about 0.6 to 7% by weight of salts comprising
    1) about 45 to 60% by weight magnesium chloride, preferably about 55 to 58%,
    2) about 29 to 41% by weight of potassium chloride, preferably about 39 to 40% by weight, and
    3) about 0 to 4% by weight of sodium chloride, preferably about 1 to 2%, and
  b) the remainder being a suitable pharmaceutically acceptable vehicle.

The composition is buffered to a pH between about 3.5 to 6.5, preferably between 3.5 and 5.5.

Advantageously, the composition can include other inorganic salts selected from the group consisting of magnesium bromide, potassium bromide, calcium bromide, calcium chloride, or a mixture thereof in an amount of about 0.5 to 4% by weight.

The composition can be in the form of a douche, gel, suppository, cream or foam.

It is therefore a general object of the invention to treat anal and/or vaginal inflammations while maintaining a proper pH.

It is another object of the invention to treat hemorrhoids.

It is still another object of the invention to provide a vaginal douche to maintain an acid environment in the vaginal cavity.

DESCRIPTION OF THE PREFERRED EMBODIMENTS

The present invention relates to a method for treatment of vaginal and/or anal inflammation. More particularly, there is provided a composition for use in the method which comprises:
 a) about 0.5 to 10% by weight, preferably about 0.6 to 7% by weight of salts comprising
  1) about 45 to 60% by weight of magnesium chloride, preferably about 55 to 58% by weight;
  2) about 29 to 41% by weight of potassium chloride, preferably about 39 to 41% by weight, and
  3) About 0 to 4% by weight of sodium chloride, preferably about 1 to 2%, and
 b) the remainder being a suitable pharmaceutically acceptable vehicle.

The composition is buffered to a pH between about 3.5 to 5.5.

The composition can include other inorganic salts selected from the group consisting of magnesium bromide, potassium bromide, calcium bromide, calcium chloride or a mixture thereof in an amount about 0.5 to 4% by weight.

The presence of chloride salts aids in cell membrane lysis. Also, chloride ions augment the antimicrobial activity of endogenous that contribute to protection against bacterial pathogens.

The acidic composition, according to the invention, may be presented in liquid and forms normally used for topical application, in particular in the form of aqueous, aqueous-alcoholic or, oil solutions, or lipophilic gels, or emulsions of liquid or semi-solid consistency of the milk type, obtained by dispersing a fatty phase in an aqueous phase (O/W) or vice versa (W/O), or of suspensions or emulsions of soft, semi-solid consistency of the gel types. These compositions are prepared according to standard methods.

They are preferably used in the form of aqueous solutions, or in the form of gels, foams, or suppositories.

The amounts of the different constituents of the compositions according to the invention are those traditionally used in the pharmaceutical field.

In a known manner, the composition of the invention may also contain adjuvants which are customary in the pharmaceutical field, such as hydrophilic or lipophilic gelling agents, hydrophilic or lipophilic active agents, preservatives, antioxidants, solvents, perfumes and fillers. The amounts of these different adjuvants are those traditionally used in the pharmaceutical or dermatological field, and are, for example from 0.01% to 10% of the total weight of the composition. Those adjuvants, depending on their nature may be introduced into the fatty phase or into the aqueous phase.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned.

Natural gums which may be used includes carageenan gum, xantham gum, alginates and gelation. As hydrophilic active agents, proteins or protein hydrolysates, amino acids, polyols, urea, allantonin, sugars and sugar derivatives, water-soluble vitamins, starch and plant extracts, in particular those of the Aloe vera may be used.

As lipophilic active agents, retinol (vitamin A) and its derivatives, tocopherol (vitamin E) and its derivatives, essential fatty acids, ceramides and essential oils may be used. These agents add extra moisturizing or skin softening features when utilized.

The compositions of the invention may include plant or herbal extracts that reduce irritation. For example, there may be utilized extracts of Paraguay tea, Kola and Guarana, which provide a source of methylxanthines, saponius, tannins, and glycosides that have been shown to be anti-inflammatory and can be used to treat irritations. The extract of Paraguay tea is known as "Mate extract" and is described in the "International Cosmetic Ingredient Dictionary", $5^{th}$ Edition. Mate extract is commercially available in combination with extracts of Koa and Guarana, which is sold by cosmetic Ingredient Resources of Stamford, Conn. under the trademark "QUENCHT".

A surfactant can be included in the composition so as to provide deeper penetration of the ingredients. Many surfactants are also antimicrobial agents, for example, nonoxynol-9 and octoxynol-p are used to prevent HIV. Generally, about 0.05 to 2.0% by weight surfactant can be used.

An example of a lubricating base which can be used is HISPAGEL a glycol-free glycerine clarthrate which is generally described as glycerin polyacrylate which is sold by Centerchem Inc. of Stamford, Conn. Generally, up to about 20% by weight of the composition comprises HISPAGEL. It can be used in combination with other gallants such as Cabopols, cellulose derivatives, clays and the like.

The preferred natural gums that can be used in amounts up to about 5% by weight include carageenan gum, xantham gum, alginates, and gelatin.

The preferred synthetic polymers that can be used include Carbopol, polyacrylic acid, polymethacrylic acid, hydroxyalkyl cellulose, methacrylate, and polyacrylamide.

The compositions may contain an additional therapeutic active agent as well as a spermicide. The additional active agent may be any of those which are approved for or used for the treatment, propylaxis, cure or mitigation of any disease of the vulva, vagina, urinary tract, cervix or other female reproductive organ or preventant of conception; for aesthetic or cosmetic usage, for diagnostic purposes; for systemic drug therapy. The agent must have utility when administered by delivery to all or a portion of the vaginal surfaces. Therapeutic active agents are normally well-known. Without being limited thereto, exemplary agents include:

Antibacterial agents such as C31G, trimethoprim, sulfamethoxazole, and chloromycetin;
antiseptic agents such as chlorhexidine gluconate;
antibiotic agents such as erythromycin, penicillins, cephalosporins and their derivatives, ampicillin, methicillin, and doxycycline;
antiparasitic agents such as thiabendazole;
antiprotozoal agents such as metronidazole, and chloroquine hydrochloride;
antiviral agents such as dextran sulfate and other sulfated polysaccharides, n-Docosanol (Lidak Pharmaceuticals), squalamine, and vidarabine;
and antifungal agents such as ketoconazole, flucytosine, itraconazole, amphotericin B, nystatin, butoconazole nitrate, and clotrimazole.

The preparations of this invention must possess a pH between 3.5 to about 5.5 and preferably between about 4 and 5.5. pH's above 6.5 are not preferred since they promote vaginal infections and inflammation. When necessary, buffers are used to adjust the pH of the system. Acceptable buffers include commonly used mixtures of a weak acid and its conjugate base, such as acetic acid and sodium acetate. Acceptable buffers may be based on inorganic salts such as phosphate and carbonate, and organic acid sodium and potassium salts such as acetate, citrate, succinate, formate, glycine, maleate, phosphates and barbiturates, with sodium citrate being preferred.

It has also been unexpectedly found that the microbial kill rate for undesirable microbes is 20 to 50 times more effective at pH's about 4.0.

The gelled compositions of this invention are formed by preparing a translucent gel of the polymer in a suitable carrier. One procedure would involve mixing the acrylic acid polymer with glycerine until the polymer is completely absorbed by the glycerine. Acceptable amounts of polymer to glycerine for this purpose may range from a ratio of 1:5 to 20 w/w. It should be recognized that other processes may be used to prepare the composition of this invention depending on the vehicle being used to prepare the gel composition and excipients employed.

As discussed above, the compositions may contain an additional therapeutic active agent as well as a spermicide. The additional active agent may be any of those which are approved for or used for the treatment, prophylaxis, cure or mitigation of any disease of the vulva, vagina, urinary tract, cervix or other female reproductive organ.

A preferred 100 ml composition of the present invention comprises:

| Ingredient | Wt. |
| --- | --- |
| Magnesium Chloride | 1.0-2.00 g |
| Magnesium Bromide | 0.01-0.05 g |
| Magnesium Sulfate | 0.01-0.05 g |
| Potassium Chloride | 0.08-1.00 g |
| Calcium Chloride | 0-0.05 g |
| Sodium Carbonate | 0-0.05 g |
| 1% Saline Solution | q.s. |

The pharmaceutical compositions may be prepared for a vaginal douche according to standard formulating procedures.

The salts may be dissolved in sterile water, physiological saline solution and buffered to a pH of 3.5 to 5.5 which is advantageously ionically balanced. A preferred buffering agent is sodium hydrogen phosphate.

It is preferred to include a preservative, for example, Thimerosal or benzalkonium chloride and/or an antioxidant, for example, vitamin E. Other filler materials which can be included are commonly found in douche or enema compositions.

The following examples illustrate the invention.

Example 1

A 100 ml solution which is effective as a vaginal douche is prepared as follows:

| Ingredient | |
| --- | --- |
| Magnesium Chloride | 3.0 mg |
| Magnesium Bromide | 0.5 mg |
| Magnesium Sulfate | 0.5 mg |
| Potassium Chloride | 3.4 mg |
| Potassium sorbate solution | 100 mg |
| Vitamin E | 0.1 mg |
| Purified Water | q.s. |

The composition is buffered to pH 4.0.

Optionally, the composition contains about 0.5% of nonoxynol-9.

Example 2

Preparation of a Gel

| Ingredients | % W/W |
| --- | --- |
| Magnesium bromide | 0.05 |
| Phytosphingosine | 0.05 |
| Magnesium Chloride | 1.6 |
| Magnesium sulfate | 0.03 |
| Carbopol 940 | 0.4 |
| Potassium Chloride | 1.0 |
| Butylene glycol | 6.5 |
| Sodium Chloride | 0.5 |
| Quench T | 3.0 |
| Chamomile glycolic extract | 3.0 |
| Sodium hydrogenphosphate | 0.5 |
| Preservative | 0.1 |
| Fragrance | 0.1 |
| Deionized Water | q.s. |
| | 100% |

To 20 ml of water with stirring, is added the Carbopol 940. The mixture is stirred until hydration is complete and then butylenes glycol is added. The remaining ingredients are mixed together and added to the first mixture. The mixing is continued until uniform. Optionally, 0.2% clotrimazole is added.

The composition may be used to treat vaginal yeast infections.

Example 3

A lubricant is prepared by admixing the following ingredients.

| Ingredients | % W/W |
| --- | --- |
| Hispagel | 20.0 |
| Magnesium Chloride | 1.2 |
| Magnesium bromide | 0.05 |
| Flax Oil | 1.0 |
| Carbopol 940 | 0.4 |
| Butylene Glycol | 6.0 |
| Potassium hydrogen phosphate | 0.1 |
| Citric Acid | 0.5 |
| Saffron | 0.2 |
| Potassium Chloride | 0.8 |
| Deionized Water | q.s. |
| | 100% |

The pH of the composition is adjusted to 4.0.

The composition can be used to treat hemorrhoids.

The invention claimed is:

1. A method for treating a patient suffering from inflammation and irritation of the vaginal cavity which comprises administering to the site of inflammation a composition having a pH between 3.5 and 5.5 consisting essentially of:
   A) about 1 to 10% by weight of salts consisting of:
      1) about 45 to 60% by weight of magnesium salts consisting of magnesium chloride, magnesium bromide and magnesium sulfate;
      2) about 20 to 40% by weight of potassium chloride;
   B) the remainder being water.

2. The method of claim 1 wherein said composition contains a gelling agent.

3. The method of claim 1 wherein said composition comprises a gel or foam.

4. The method of claim 1 wherein said composition is a vaginal douche.

5. The method of claim 1 wherein said patient is suffering from a vaginal yeast infection.

6. The method of claim 1 wherein 100 ml of said composition consists of:

| Ingredient | Wt. |
| --- | --- |
| Magnesium Chloride | 1.0-2.00 g |
| Magnesium Bromide | 0.01-0.05 g |
| Magnesium Sulfate | 0.01-0.05 g |
| Potassium Chloride | 0.08-1.00 g |
| Calcium Chloride | 0-0.05 g |
| Sodium Carbonate | 0-0.05 g |
| water. | q.s. | said composition having a pH of 3.5 to 5.5.

7. The method of claim 6 including in said composition a surfactant.

* * * * *